US007659088B2

(12) United States Patent
Elhammer

(10) Patent No.: US 7,659,088 B2
(45) Date of Patent: Feb. 9, 2010

(54) ASSAY FOR INOSITOL PHOSPHORYLCERAMIDE SYNTHASE ACTIVITY

(75) Inventor: Ake Elhammer, Kalamazoo, MI (US)

(73) Assignee: AureoGen Biosciences, Inc., Kalamazoo, MI (US)

( * ) Notice: Subject to any disclaimer, the term of this patent is extended or adjusted under 35 U.S.C. 154(b) by 435 days.

(21) Appl. No.: 11/805,010

(22) Filed: May 22, 2007

(65) Prior Publication Data

US 2007/0269844 A1 Nov. 22, 2007

Related U.S. Application Data

(60) Provisional application No. 60/802,479, filed on May 22, 2006.

(51) Int. Cl.
*C12Q 1/48* (2006.01)
*C12N 9/12* (2006.01)
*G01N 21/64* (2006.01)

(52) U.S. Cl. .......................... 435/15; 435/194; 436/172
(58) Field of Classification Search ....................... None
See application file for complete search history.

(56) References Cited

U.S. PATENT DOCUMENTS

| 5,976,866 A | 11/1999 | Heidler et al. |
| 6,022,684 A | 2/2000 | Radding et al. |
| 6,197,928 B1 * | 3/2001 | Tsien et al. .................. 530/350 |
| 6,596,499 B2 * | 7/2003 | Jalink .......................... 435/7.1 |
| 6,808,892 B1 | 10/2004 | Schnell et al. |
| 7,105,636 B1 * | 9/2006 | Wrana .......................... 530/350 |
| 2005/0048563 A1 * | 3/2005 | Jalink .......................... 435/7.1 |
| 2006/0112440 A1 * | 5/2006 | Tsien et al. ................... 800/18 |
| 2007/0111270 A1 * | 5/2007 | Zhang et al. ................... 435/8 |

FOREIGN PATENT DOCUMENTS

| WO | WO-98/46639 | 10/1998 |
| WO | WO 00/18949 A2 * | 4/2000 |

OTHER PUBLICATIONS

Aeed, Paul A., et al, Effect of Membrane Perturbants on the Activity and Phase Distribution of Inositol Phophorylceramide Synthase; Development of a Novel Assay, *Biochemistry* 2004, 43, 8483-8493, American Chemical Society.
Figueiredo, Juliana M., et al, Characterization of the inositol phosphorylceramide synthase activity from *Trypanosoma cruzi*, *Biochem. J.* (2005) 387, 519-529.

(Continued)

*Primary Examiner*—Anand U Desai
*Assistant Examiner*—William W Moore
(74) *Attorney, Agent, or Firm*—Honigman Miller Schwartz and Cohn LLP; Kelly T. Murphy; Jonathan P. O'Brien

(57) ABSTRACT

Disclosed is a simple and reproducible method for assaying inositol phosphorylceramide synthase activity that employs a fluorescence resonance energy transfer pair for measuring enzyme activity. The invention also includes a novel method for identifying IPC synthase inhibitors.

13 Claims, 4 Drawing Sheets

OTHER PUBLICATIONS

Fischl, Anthony S., et al, Inositolphosphoryl Ceramide Synthase from Yeast, *Methods In Enzymology*, vol. 311, 123-130, Academic Press.

Mandala, Suzanne M., et al, Khafrefungin, a Novel Inhibitor of Sphingolipid Synthesis, *The Journal of Biological Chemistry*, vol. 272, No. 51, Issue of Dec. 19, pp. 32709-32714, 1997, The American Society for Biochemistry and Molecular Biology, Inc.

Mandala, Suzanne M., et al, Rustmicin, a potent Antifungal Agent, Inhibits Sphingolipid Synthesis at Inositol Phosphoceramide Synthase, *The Journal of Biological Chemistry*, vol. 273, No. 24, Issue of Jun. 12, pp. 14942-14949, 1998, The American Society of Biochemistry and Molecular Biology, Inc.

Nagiec, M. Marek, et al, Sphingolipid Synthesis as a Target for Antifungal Drugs, *The Journal of Biological Chemistry*, vol. 272, No. 15, Issue of Apr. 11, pp. 9809-9817, 1997, The American Society for Biochemistry and Bolecular Biology, Inc.

Zhong, Wenyan, et al, Inhibition of yeast inositol phosphorylceramide synthase by aureobasidin, a measured by a fluorometric assay, *FEBS Letters* 463 (1999) 241-244, Federation of European Biochemical Societies.

\* cited by examiner

ASSAY FOR INOSITOL PHOSPHORYLCERAMIDE SYNTHASE ACTIVITY

This application claims priority to U.S. Ser. No. 60/802,479 filed on May 22, 2006.

FIELD OF THE INVENTION

The invention relates to the field of antifungal agents, to methods for the identification and characterization of compounds with the potential to be developed into antifungal drugs. More specifically, the invention relates to methods for screening for inhibitors of inositol phosphorylceramide synthase (IPC synthase).

BACKGROUND OF THE INVENTION

The incidence of life-threatening fungal infections is increasing at an alarming rate. With the exception of Staphylococci infections, the fungus C. albicans represents the fastest growing area of concern in hospital acquired infections. About 90% of nosocomial fungal infections are caused by species of Candida with the remaining 10% being attributable to Aspergillus, Cryptococcus, and Pneumocystis. While antifungal compounds with some efficacy have been developed, progress in discovery of new antifungal compounds has been slow and lags far behind the rapid growth in the incidence of systemic fungal infections. (See e.g. WO 2004/050685 PCT/US2003/038595 and references therein; Abi-Said et al., 1996; Rees et al., 1998.) This is because of the innate difficulties of finding selective inhibitors for one large group of eukaryotes (fungi) invading another (humans). As a consequence, the current antifungal drug market is dominated by only two classes of drugs, polyenes and azoles, both of which have significant limitations, in terms of efficacy, toxicity, problems with drug-drug interactions and the generation of resistant organisms (e.g. Rex et al., 1995; Hay, 2003). Hence, there is an urgent need for new antifungal compounds with novel modes of action.

Inositolphosphoryl ceramides are sphingolipids found in a number of fungi including but not limited to all major human pathogens (Lester and Dickson, 1993; Vincent and Klig, 1995; Dickson and Lester, 1999). Organisms such as C. albicans, A. fumigatus, C. neoformans and H. capsulatum all contain inositolphosphoryl ceramides, as does S. cerevisiae, S. pombe, and N. crassa. The inositolphosphoryl ceramide biosynthesis pathway in fungi involves at least eight separate reactions, each catalyzed be a specific enzyme. The first five steps in the pathway, starting with the assembly of 3-ketohydrosphingosine, by the enzyme serine palmitoyltransferase, and ending with the hydroxylation of ceramide, by ceramide hydroxylase, are quite similar to the corresponding steps in the mammalian sphingolipid biosynthesis pathway (Nagiec et al., 1997; Dickson and Lester, 1999). Consistent with this, it has been found that inhibitors targeting these reactions have close to equal efficacy towards fungi and mammalian cells and, consequently, such compounds have little potential for development into antifungal drugs. However, the sixth reaction step is unique to fungi and plants. In this step the enzyme IPC synthase catalyzes the transfer of inositol phosphate from phosphatidyl inositol, to ceramide, to form inositol phosporylceramide (FIG. 1). Genetic and mutational studies have demonstrated that this reaction is essential in fungi (Nagiec et al., 1997). It has also been shown, in several organisms, that inhibition of this reaction step is cidal (e.g. Takesako et al., 1993; Endo et al., 1997). By contrast, it has also been demonstrated that the two to three downstream (from IPC synthase) reaction steps, in the fungal sphingolipid biosynthesis pathway, are not essential (Dickson and Lester, 1999).

The uniqueness of the fungal IPC synthase (IPCS) catalyzed reaction, coupled with the fact that the enzyme is essential in fungi, make IPC synthase an attractive target for antifungal drugs. Further supporting this notion is the recent identification of several very potent natural antifungal compounds that all target IPC synthase (e.g., Mandala 1997, Mandala 1998, Zhong 1999, Kurome 2000). Some of these compounds have demonstrated therapeutic activity in animal models, even when delivered orally (Takesako 1993).

In view of the foregoing, inositol phosphorylceramide (IPC) synthase is an important enzyme in fungi and compounds capable of specifically inhibiting this enzyme would have considerable potential to be developed into antifungal drugs and hence meet an immediate, unmet medical need.

A significant impediment to the identification of novel IPC synthase inhibitors with drug candidate potential, is the lack of an assay suitable for robotized screening of large compound libraries (high-throughput screening). Currently used assays are complicated, labor intense and generate poorly reproducible data (e.g. Mandala et al., 1997; Mandala et al., 1998; Ko et al., 1995; Fischl et al., 1999; Aeed et. al., 2004). As such they are completely unsuitable for high-throughput screening efforts.

SUMMARY OF THE INVENTION

This invention provides a method for assaying inositol phosphoceramide synthase (IPC synthase) activity that is easy to perform, reproducible and fully compatible with robotized high-throughput screening procedures.

The invention further comprises a novel methodology for screening, and other efforts aimed at identifying IPC synthase inhibitors with the potential of becoming antifungal drugs.

In one aspect, the invention includes a method for measuring inositol phosphorylceramide (IPC) synthase activity, which includes providing a sample containing inositol phosphorylceramide synthase, adding a fluorescent labeled IPC synthase substrate, adding a phosphate binding compound conjugated to a fluorophor, wherein the phosphate binding compound conjugated to a flurorphor forms a FRET pair with the fluorescent labeled IPC synthase substrate, and measuring fluorescence.

In a second aspect, the invention provides a method for identifying inositol phosphorylceramide synthase inhibitors, which includes providing a sample containing inositol phosphorylceramide synthase, adding a test compound to the sample, adding a fluorescent labeled IPC synthase substrate, adding a phosphate binding compound conjugated to a fluorophor, wherein the phosphate binding compound conjugated to a flurorphor forms a fluorescence resonance energy transfer (FRET) pair with the fluorescent labeled IPC synthase substrate; and measuring fluorescence.

In a third aspect, the invention provides a kit that includes a fluorescent labeled IPC synthase substrate and a phosphate binding compound conjugated to a fluorophor, wherein the phosphate binding compound conjugated to a flurorphor forms a FRET pair with the fluorescent labeled IPC synthase substrate. In one embodiment the kit further includes a sample containing inositol phosphorylceramide synthase. In another embodiment the kit further comprises phosphatidyl inositol, and in yet another embodiment, the kit further comprises a known modulator of IPC synthase.

Specific embodiments of the foregoing aspects of the invention may include one or more of the following. The fluorescent labeled IPC synthase substrate is a fluorescent labeled ceramide. The fluorescent labeled ceramide is selected from the group consisting of C5-NBD-ceramide (5-((N-(7-nitrobenz-2-oxa-1,3-diazol-4-yl)amino)hexanoyl) sphingosine), C6-NBD-ceramide (6-((N-(7-nitrobenz-2-oxa-1,3-diazol-4-yl)amino)hexanoyl)sphingosine), C12-NBD-ceramide (12-((N-(7-nitrobenz-2-oxa-1,3-diazol-4-yl) amino)hexanoyl)sphingosine), BODIPY-FL-C5-ceramide (N-(4,4-difluoro-5,7-dimethyl-4-bora-3a,4a-diaza-s-indacene-3-pentanoyl)sphingosine), BODIPY-FL-C6-ceramide and BODIPY-TR-C6-ceramide (N-((4-(4;4-difluoro-5-(2-thienyl)-4-bora-3a,4a-diaza-s-indacene-3-yl)phenoxy) acetyl)sphingosine); all of which are available from Invitrogen, (Molecular Probes). The fluorescent labeled ceramide is C6-NBD-ceramide. The phosphate binding compound includes a peptide that has at least one positively charged amino acid. The phosphate binding compound includes a peptide that has one or more of arginine, histidine and lysine. The phosphate binding compound includes a hexapeptide. The fluorophor conjugated to the phosphate binding compound is selected from the group consisting of Alexa Fluor 350, anilinonaphthalene, dansyl, dapoxyl, dibromobimane, diethylaminocoumarin, dimethylaminocoumarin, dimethylaminonaphthalene, monobromobimane, monochlorobimane, naphthalene, pyrene, stilbene and D-346. The fluorescent labeled substrate is C6-NBD-ceramide and the fluorophor conjugated to the phosphate binding compound is D-346. The sample containing inositol phosphorylceramide synthase is derived from fungal cells.

DEFINITIONS

A Fluorescence Resonance Energy Transfer (FRET) pair consists of two fluorophors wherein the absorption (or excitation) spectrum of one fluorophor overlaps the fluorescence emission spectrum of the second fluorophor.

As used herein, an inositol phosphorylceramide (IPC) synthase substrate is a compound to which IPC synthase binds and transfers a phosphate containing group.

As used herein, a "test compound" refers to a substance such as a chemical compound (naturally occurring or synthesized) such as a biological macromolecule, such as a nucleic acid (e.g., DNA, RNA antisense RNA, siRNA, and ribozymes), peptide, polypeptide, peptidomimetic, protein, non-peptide, antibody or fragment thereof, lipid, carbohydrate, small molecule, organic molecule, other drug or an extract made from biological materials such as bacteria, plants, fungi or animal cells or tissues, or an inorganic element or molecules.

As used herein, a "sample" includes any material that contains the enzyme IPC synthase. For example, a sample can be an extract or microsomal membranes prepared from any fungal cells, including, without limitation, *Candida, Aspergillus, Cryptococcus, Saccharomyces, Neurospora, Histoplasmosis, Neurospora* and *Pneumocystis*. A sample can also be an extract or microsomal fraction from *Trypanosoma cruzi* or other protozoans or life forms that have IPC synthase activity (Figueiredo, et al. 2005). The sample can also be prepared from plants or plant cells. A sample can also be purified IPC synthase or partially purified IPC synthase.

Abbreviations

NBD, 4-nitrobenzo-2-oxa-1,3-diazole
BODIPY, 8-methyl-4,4-difluoro- 1,3,5,7-tetramethyl 14-bora-3a,4a-diasa-3-indacene
FRET, Fluorescence Resonance Energy Transfer
IPC, Inositol phosphorylceramide

DETAILED DESCRIPTION OF THE INVENTION

Figure 1:
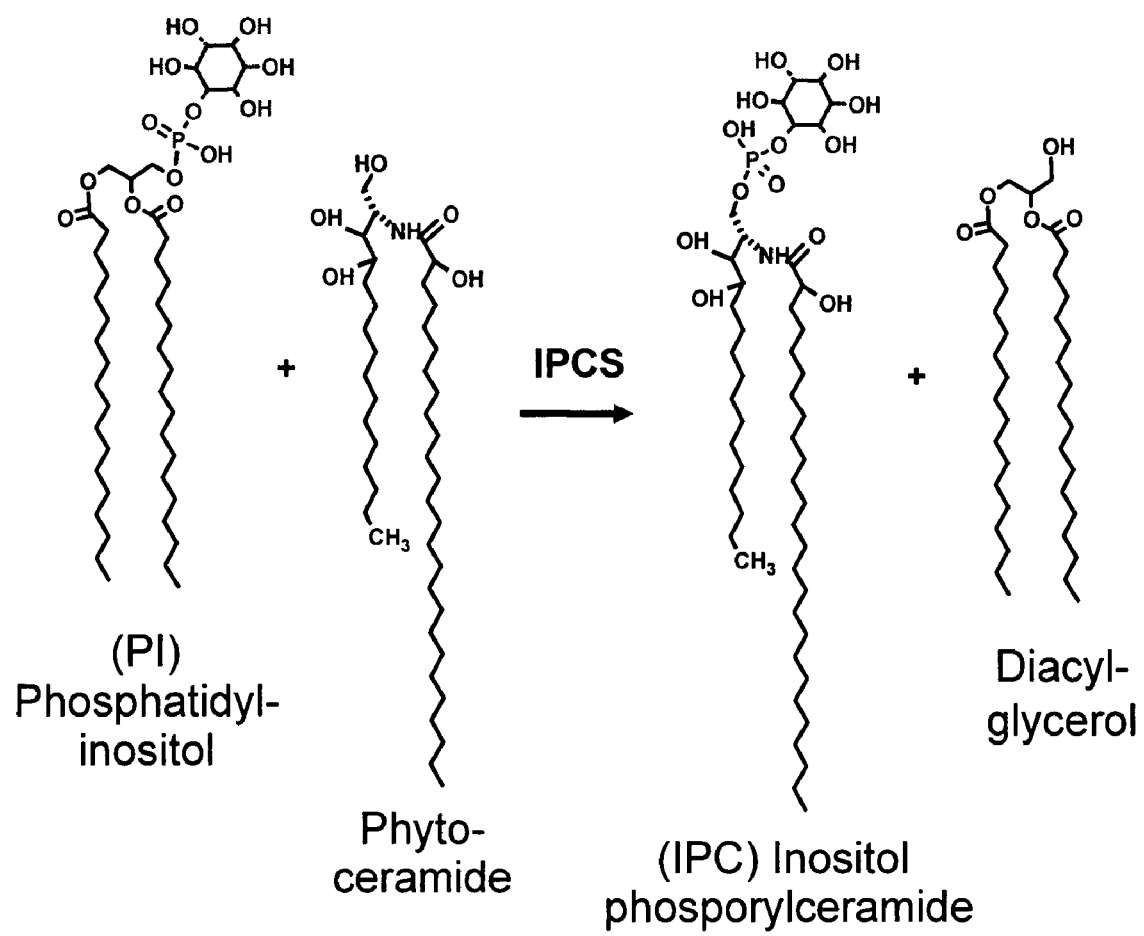
FIG. 1 is a schematic representation of the reaction catalyzed by IPC synthase.
Figure 2:
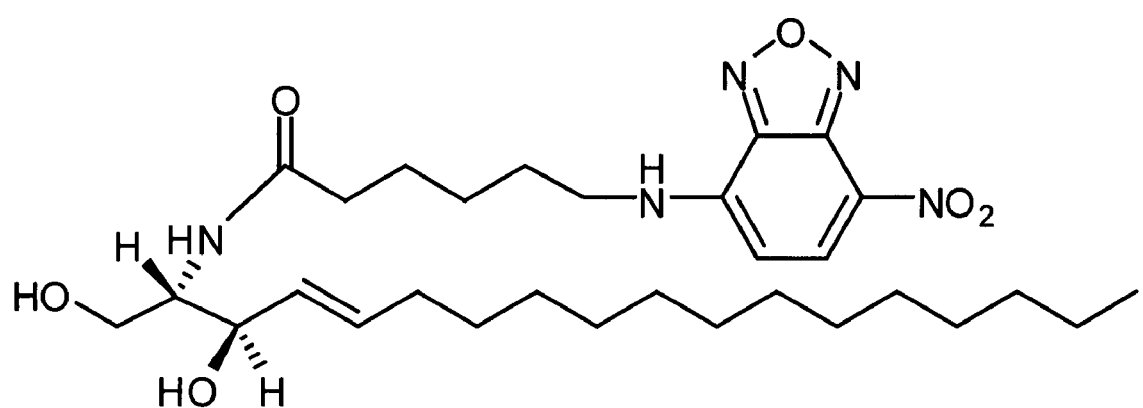
FIG. 2 shows the chemical structure of $C_6$-NBD-ceramide.

Current assays for IPC synthase activity involve incubating phosphatidylinsitol and $C_6$-N-[7-(4-nitrobenzo-2-oxa-1,3-diazole)]-ceramide ($C_6$-NBD-ceramide; FIG. 2), or radioactive ceramide, with an enzyme preparation, for a certain period of time. The reaction product, $C_6$-NBD-inositol phosphorylceramide (IPC), is subsequently separated from unreacted $C_6$-NBD-ceramide by adsorbing onto 100 μl (sedimented gel volume) AG4-X4 resin, formate form, in a 96-well filter plate, using a vacuum manifold. Following adsorption, the resin is washed five times with 200 μl of 96% (v/v) methanol and the product eluted with 200 μl of 1.0 M potassium formate in 96% (v/v) methanol. The product is then quantified in a fluorescence plate reader, using 466 ηm excitation wave-length and measuring emission at 536 ηm. Different enzyme preparations have been used for this and other (earlier) IPC synthase assays, resulting in data of varying quality (e.g., Ko et al., 1994; Ko et al., 1995; Mandala et al., 1997; Mandala, et al., 1998; Fischl et al., 1999; Zhong et al., 1999; Heidler and Radding, 2000). Recently, changes in the procedure used for preparation of the enzyme drastically improved the performance of this type of IPC synthase assay and transformed it from an assay procedure generating poorly reproducible and at best qualitative data, into a reliable, reproducible assay capable of actually generating kinetic parameters (Aeed et al. 2004).

Still, a remaining weakness associated with the assay system developed by Aeed et al. (2004) is the complex product work-up procedure. Consistently pipetting (exact amounts of) ion-exchange resin into 96-well plates is difficult. And the many manipulations required for the product work-up make the assay labor-intensive. Hence, generating consistent, reproducible data (with this assay system) is challenging. It depends to a large extent on the skill of the individual carrying out the work, and the assay is virtually impossible to robotize for use in high-throughput screening efforts.

Figure 3:
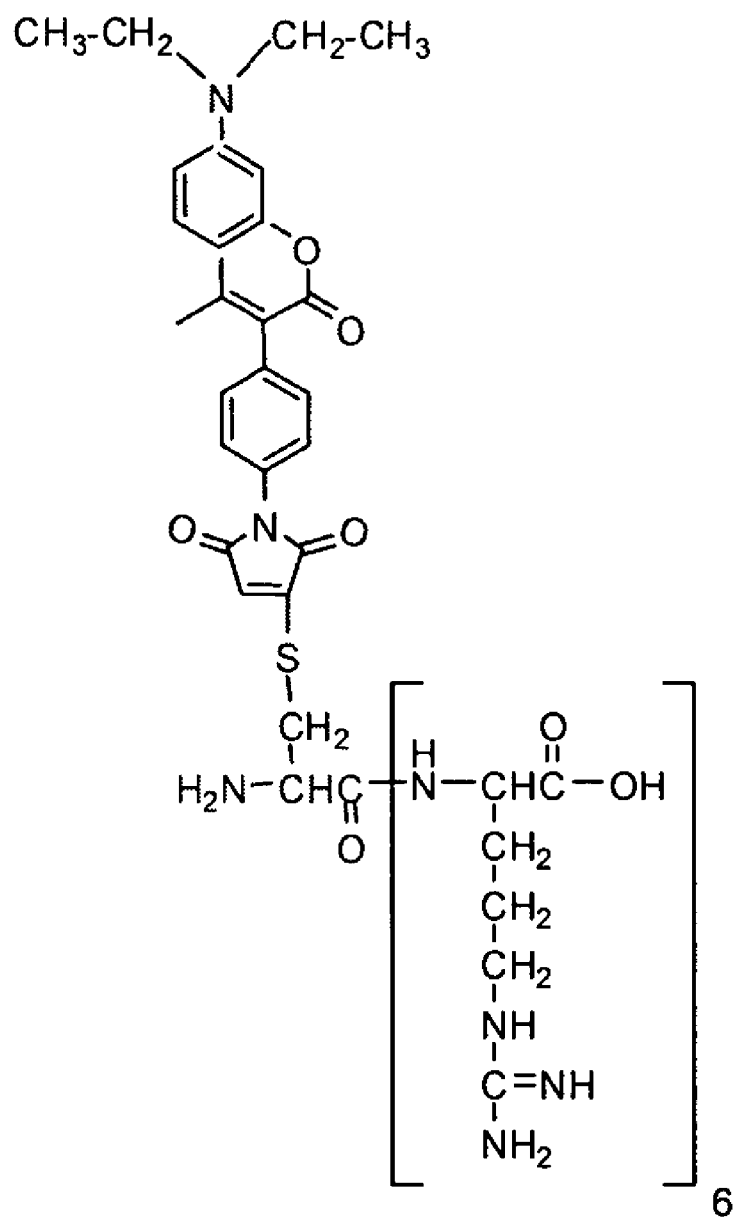
FIG. 3 illustrates an example of the detection and quantification of reagents functional in the IPC synthase FRET assay. The reagent comprises the fluorophor D-346 conjugated to a peptide composed of six arginine residues [in brackets].
Figure 4:
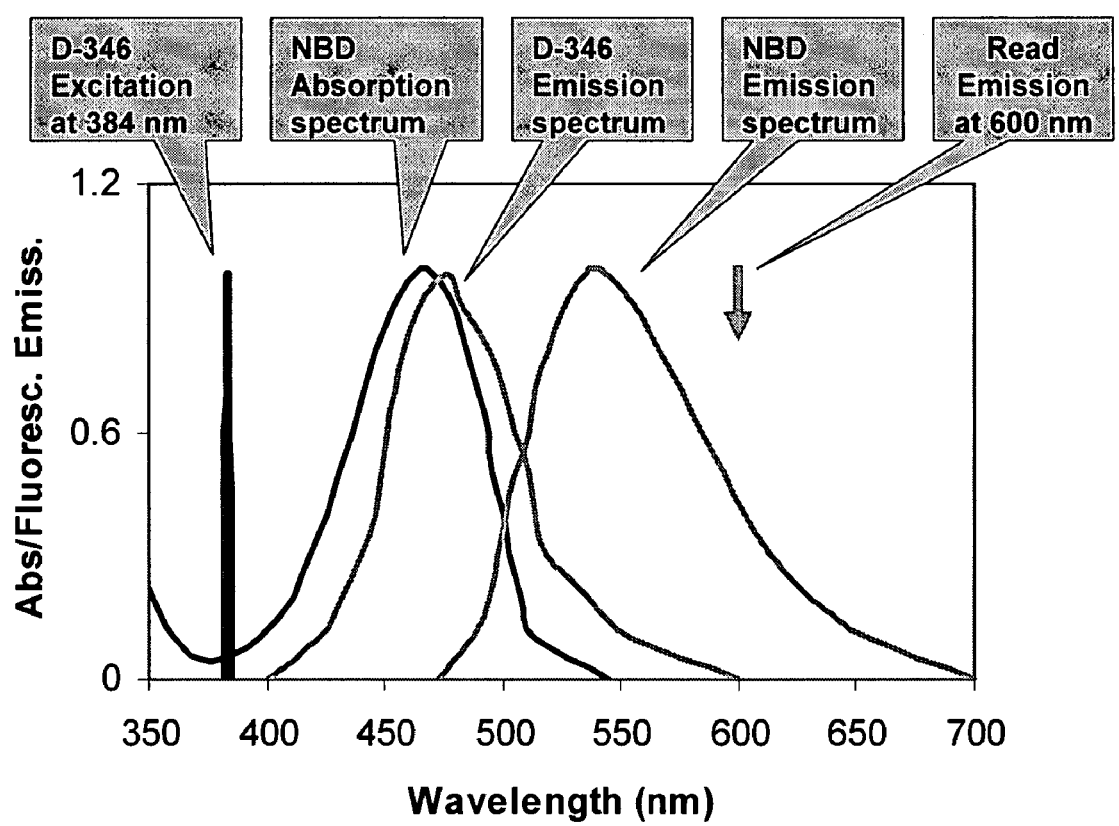
FIG. 4 is a graph of absorption and emission spectra of examples of fluorophors (FRET pairs) that can be used in IPC synthase FRET assay. The graph includes absorption and emission spectra of NBD, emission spectrum of D-346, and examples of excitation and emission read wavelengths for the D-346/NBD FRET pair.

An assay of this invention and described herein circumvents the current problems with the IPC assay product work-up. The assay of this invention includes reacting phosphatidylinositol with $C_6$-NBD-ceramide in the presence of a detergent treated enzyme preparation. The resulting assay product does not have to be isolated for quantification. Instead, at the completion of the enzymatic reaction, a poly-arginine peptide (or other phosphate-binding compound) conjugated to a fluorophor (FIG. 3), is added to the reaction mixture. The poly-arginine peptide (or other phosphate-binding compound) binds to the phosphate group in the reaction product ($C_6$-NBD-inositol phosphorylceramide). This brings the fluorophor (linked to the peptide or other phosphate-binding compound) in close proximity to the fluorescent NBD tag on the ceramide portion of the reaction product. One flurophor that can be used is the 7-diethylamino-3-(4'-maleimidylphenyl)-4-methylcoumarin [D-346]-hexa-arginine conjugate (shown in FIG. 3) on the peptide (or compound). The fluorophor is chosen such that it has an emission spectrum that to a very large extent overlaps the excitation spectrum of NBD. Consequently, the two fluorescent moieties forms a "fluorescent energy transfer" (FRET) pair, i.e. the emitted radiation from the higher energy fluorophor (e.g. D-346) serves as excitation radiation for the lower energy moiety (e.g. NBD) (FIG. 4). And when the reaction mixture (following addition of the fluorophor-conjugated polyarginine peptide) is illuminated at the excitation wavelength of the polyarginine peptide-conjugated fluorophor, a fluorescence signal, proportional to the amount of reaction product in the mixture, will be emitted at the emission wave-length of NBD. In practical terms, this means that the amount of product formed in the assay can be quantified directly in the 96-well (or 384-well) assay plate, without separation from the reaction mixture or any other work-up, using a 96-well plate fluorescence reader. Hence, an assay comprising this product quantification method is readily adaptable to robotized high-throughput screening efforts.

An additional advantage of the FRET-based assay is that the FRET signal used for quantification of the reaction product is quite specific. It will be generated only if the two fluorescent moieties are brought in close proximity of each other, i.e., the fluorophor-conjugated peptide (or other fluorophor-conjugated phosphate-binding compound) by itself does not generate this signal, nor does it generate a signal if bound to any other molecule than the NBD-tagged reaction product. Hence, the data scatter caused by variations in the sample work-up in existing assays, is eliminated.

Different lengths and composition (number of arginine residues) can be used for the polyarginine peptide. Moreover, other (positively) charged amino acids, such as for instance lysine or histidine, may also be used in the peptide, either exclusively or in combination with different charged or uncharged amino acids, including arginine. The amino acids can be any amino acids, including naturally occurring and non-naturally occurring and modifications and derivatives thereof. The length and composition of the peptide is chosen such that adhesion to the reaction product is maximized and non-specific binding (to other molecules) is minimized. A peptide containing six arginine residues (FIG. 3) is functional. In addition, other compounds, with charged functionalities capable of binding to phosphate groups may be used instead of a peptide.

Different fluorophors may be attached, at either end, to the peptide or other phosphate-binding molecule, using known methods. These fluorophors may have an emission spectrum that partly or completely overlaps the excitation (or absorption) spectrum of the fluorophor conjugated to ceramide. If an NBD-conjugated ceramide, such as $C_6$-NBD-ceramide, is used, a functioning example of such a compound is D-346 (FIG. 4). Alternatively, the fluorophor conjugated to the phosphate-binding peptide (or other phosphate-binding compound) may have an excitation spectrum that partly or completely overlaps the emission spectrum of NBD (or other fluorophor conjugated to ceramide). Some non-limiting examples of thiol-reactive fluorophors, i.e. fluorophors that are easily conjugated to a synthetic peptide are listed in Table 1.

TABLE 1

Examples of Commercially Available Thiol-Reactive Fluorescent Compounds

| Compound | Abs Max (ηm) | Em Max (ηm) |
|---|---|---|
| Alexa Fluor 350 | 346 | 442 |
| Anilinonaphtalene | 326 | 462 |
| Dansyl | 328 | 563 |
| Dapoxyl | 374 | 572 |
| Dibromobimane | 394 | 490 |
| Diethylaminocoumarin | 384 | 470 |
| Dimethylaminocoumarin | 394 | 465 |
| Dimethylaminonaphtalene | 391 | 500 |
| Monobromobimane | 394 | 490 |
| Monochlorobimane | 394 | 490 |
| Naphtalene | 336 | 490 |
| Pyrene | 339 | 384 |
| Stilbene | 329 | 408 |

Provided the fluorescence characteristics of the fluorophor conjugated to ceramide are matched to the fluorophor conjugated to the peptide (or other phosphate-binding compound), such that a FRET pair is formed, ceramide-fluorophor conjugates other than $C_6$-NBD-ceramide can also be used in the assay. Non-limiting examples of commercially available ceramide-fluorophor conjugates are listed in Table 2. However, it is important to realize that chemistry approaches suitable for conjugation of a range of different lipid-compatible fluorophors, to ceramide, are readily available. Hence, a number of fluorophors, in addition to the two used for the compounds listed in Table 2, can be used and the only significant requirement for the fluorophor conjugated to ceramide, is that it is capable of forming an efficient FRET pair with the fluorophore used on the assay detection and quantification peptide or other compound. A few non-limiting examples of fluorophors that likely would work with a D-346-containing peptide (or other detection compound) when conjugated to ceramide are Alexa Fluor, Fluorescein, Lucifer Yellow, Oregon Green and PyMPO (1-(3-(succinimidyloxycarbonyl) benzyl)-4-(5-(4-methoxyphenyl)oxazol-2-yl)pyridinium bromide).

TABLE 2

Examples of Commercially Available Fluorophor-Conjugated Ceramides

| Compound | Abs Max (ηm) | Em Max (ηm) |
|---|---|---|
| $C_5$-NBD-ceramide | 478 | 541 |
| $C_6$-NBD-ceramide | 478 | 541 |
| $C_{12}$-NBD-ceramide | 478 | 541 |
| BODIPY FL $C_5$-ceramide | 505 | 513 |
| BODIPY FL $C_6$-ceramide | 505 | 513 |
| BODIPY TR $C_6$-ceramide | 544 | 570 |

The assay comprises incubating a sample with a fluorescent labeled IPC synthase substrate and adding a phosphate binding compound conjugated to a fluorophor, wherein the phosphate binding compound conjugated to a fluorophor forms a FRET pair with the fluorescent labeled IPC synthase substrate. The sample can be any material that contains IPC synthase.

The assay can be used to identify an IPC synthase modulator. The modulator can inhibit or activate IPC synthase. A test compound can be added to the assay to determine whether it modulates IPC synthase activity. Known modulators of activity can be used as controls or used for comparison of test compounds. Known inhibitors include, without limitation, Aureobasidin A (Nagiec, et. al. 1997), galbonolide A or rustmicin (Mandala, et al. 1998), and khafrefugen (Mandala, et al. 1997).

The present invention also provides kits for assaying IPC synthase activity and for testing compounds for modulating IPC synthase activity. The kits can include reagents for performing the assay including one or more of: (1) a fluorescent labeled IPC synthase substrate, (2) a phosphate binding compound conjugated to a fluorophor, wherein the phosphate binding compound conjugated to a fluorophor forms a (FRET) pair with the fluorescent labeled IPC synthase substrate, (3) phosphatidyl inositol, (4) a sample that contains IPC synthase, (5) a known modulator of IPC synthase, (6) buffers and other reagents, including, for example, phosphate buffer, and CHAPS and (7) vessels in which to perform the assay.

EXAMPLE

Assay Procedure

The conditions described by Aeed et al. (2004) are used to isolate 10 μg (protein) of CHAPS-washed membranes which is then pre-incubated with 4 ηmoles of phosphatidylinositol (PI) in 28 μl 71.4 mM potassium phosphate buffer, pH 7.0 for 30 min in a 96-well plate. The enzymatic reaction is subsequently started by addition of 12 μl of 0.1 mg/ml $C_6$-NBD-ceramide, in ethanol, or 2 mM CHAPS. Final assay volume is 40 μl and final reagent concentrations are 50 mM potassium phosphate, pH 7.0, 0.25 mg membrane protein/ml, 5 μM $C_6$-NBD-ceramide, 100 μM PI, 0.3% (v/v) ethanol and 0.6 mM CHAPS. Following incubation at room temperature for 5-30 min, the reaction is stopped by adding 150 μl 96% (v/v) methanol. 150 μl 100 μM D-346-hexa-arginine in 50 mM potassium phosphate, pH 7.0, is added, and the plate is incubated at room temperature for 5 minutes. Fluorescence is subsequently measured at 600 ηm, using an excitation wavelength of 384 ηm.

The assay may be scaled up or down, using different volumes appropriately. The assay may also be carried out in any suitable vessel, including plates containing multiple wells, including two up to 384 or more well plates, microscope slides, or other vessels.

Other Embodiments

The foregoing example and description are not meant to limit the invention. While the invention has been described in terms of different specific embodiments and examples, those skilled in the art will recognize that various changes and modifications can be made through routine experimentation without departing from the spirit and scope of the invention. Accordingly, the invention should be understood as not being limited by the foregoing detailed description, but as being defined by the appended claims and their equivalents.

REFERENCES

The following patent documents and journal articles are hereby incorporated by reference in their entirety.

Patent Documents:
WO 2004/050685 PCT/US2003/038595

Journal Articles:
Abi-Said, D., Anaissie, E., Uzun, O., Raad, I., Pinzcowski, H., and Vartivarian, S. (1997) *Clin. Infect. Diseases* 24, 1122-1128.

Aeed, P. A., Sperry, A. E., Young, C. L., Nagiec, M. M., and Elhammer, A. P. (2004). *Biochemistry*, 43, 8483-93.

Dickson, R. C. and Lester, R. L. (1999) *Biochim. Biophys. Acta* 1426, 347-357.

Endo, M., Takesako, K., Kato, I., and Yamaguchi, H., (1997) *Antimicrob. Agents. Chemother.*, 41, 672-676.

Figueiredo, J. M., Dias, W. B., Mendonca-Previato, L., Previato, J. E. and Heise, N. (2005) *Biochem. J.*, 387, 519-529.

Fischl A. S, Liu, Y., Browdy A, Cremesti A. E. (1999) *Meth. Enzymol.* 311, 123-130.

Hay, R. J. (2003) *Dermatol. Clin.* 212, 577-587.

Heidler, S. A., and Radding, J. A. (2000) *Biochim. Biophys. Acta.* 1500, 147-152.

Ko, J., Cheah, S., and Fischl, A. S. (1994) *J. Bacteriol.* 176, 5181-5183.

Ko J., Cheah, S., Fischl A. S. (1995) *J. Food. Biochem.* 19, 792-267.

Kurome T, and Takesako, K. (2000) *Curr. Opin. Anti-infect. Invest. Drugs* 2, 375-386

Lester, R. L., and Dickson, R. C. (1993) *Adv. Lipid Res.* 26, 253-274.

Mandala, S. M., Thornton, R. A., Rosenbach, M., Milligan, J., Garcia-Calvo, M., Bull, H. G., and Kurtz, M. B. (1997) *J. Biol. Chem.* 272, 32709-32714.

Mandala, S. M., Thornton, R. A., Milligan, J., Rosenbach, M., Garcia-Calvo, M., Bull, H. G., Harris, G., Abruzzo, G. K., Flattery, A. M., Gill, C. J., Bartizal, K., Dreikorn, S., and Kurtz, M. B. (1998) *J. Biol. Chem.* 273, 14942-14949.

Nagiec, M. M, Nagiec, E. E., Baltisberger, J. A., Wells, G. B., Lester, R. L., and Dickson, R. C. (1997) *J. Biol. Chem.* 272, 9809-9817.

Rees, J. R., Pinner, R. W., Hajjeh, R. A., Brandt, M. E., and Reingold, A. L. (1998) *Clin. Infect. Diseases* 27, 1138-1147.

Rex, J. H., Rinaldi, M. G., and Pfaller, M. A. (1995) *Antimicrob. Agents Chemother.* 39, 1-8.

Takesako, K., Kuroda, H., Inoue, T., Haruna, F., Yoshikawa, Y., Kato, I., Uchida, K., Hiratani, T., and Yamaguchi, H. (1993) *J. Antibiot. (Tokyo)* 46, 1414-1420.

Vincent, V. L., and Klig, L. S. (1995) *Microbiology* 141, 1829-1837.

Zhong, W., Murphy, D. J., and Georgopapadakou, N. H. (1999) *FEBS Lett.* 463, 241-244.

What is claimed is:

1. A method for measuring inositol phosphorylceramide (IPC) synthase activity comprising:
    a) providing a sample containing inositol phosphorylceramide synthase and phosphatidyl inositol;
    b) providing a fluorescent labeled IPC synthase substrate that is a fluorescent labeled ceramide;
    c) providing a phosphate binding peptide comprising at least one positively charged amino acid wherein the peptide is conjugated to a fluorophor which forms a fluorescence resonance energy transfer (FRET) pair with the fluorescent labeled IPC synthase substrate, and
    d) measuring fluorescence in the sample,
    whereby IPC synthase activity is measured.

2. The method of claim 1, wherein the phosphate binding peptide comprises one or more of arginine, histidine and lysine.

3. The method of claim 1, wherein the phosphate binding peptide comprises a hexapeptide.

4. The method of claim 1, wherein the fluorescent labeled ceramide is selected from the group consisting of C5-NBD-ceramide, C6-NBD-ceramide, C12-NBD-ceramide, BODIPY-FL-C5-ceramide, BODIPY-FL-C6-ceramide and BODIPY-TR-C6-ceramide.

5. The method of claim 1 wherein the fluorescent labeled ceramide is C6-NBD-ceramide.

6. The method of claim 1 wherein the fluorophor conjugated to the phosphate binding peptide is selected from the group consisting of Alexa Fluor 350, anilinonaphthalene dansyl, dapoxyl, dibromobimane, diethylaminocoumarin, dimethylaminocoumarin, dimethylaminonaphthalene, monobromobimane, monochlorobimane, naphthalene, pyrene, stilbene and D-346.

7. The method of claim 1 wherein the fluorophor conjugated to the phosphate binding peptide is D-346.

8. The method of claim 1 wherein the fluorescent labeled substrate is C6-NBD-ceramide and the fluorophor conjugated to the phosphate binding peptide is D-346.

9. The method of claim 1 wherein the sample containing inositol phosphorylceramide synthase is derived from fungal cells.

10. A method for identifying inositol phosphorylceramide synthase inhibitors comprising
    a) providing a sample containing inositol phosphorylceramide synthase and phosphatidyl inositol;
    b) providing a test compound to the sample;
    c) providing a fluorescent labeled PC synthase substrate that is a fluorescent labeled ceramide;
    d) providing a phosphate binding peptide comprising at least one positively charged amino acid wherein the peptide is conjugated to a fluorophor which forms a fluorescence resonance energy transfer (FRET) pair with the fluorescent labeled IPC synthase substrate, and
    e) measuring fluorescence in the absence of the test compound and in the presence of the test compound,
    whereby an IPC synthase inhibitor is identified.

11. A kit comprising
    a) a fluorescent labeled PC synthase substrate that is a fluorescent labeled ceramide,
    b) phosphatidyl inositol, and
    c) a phosphate binding peptide comprising at least one positively charged amino acid wherein the peptide is conjugated to a fluorophor capable of forming a fluorescence resonance energy transfer (FRET) pair with the fluorescent labeled IPC synthase substrate.

12. The kit of claim 11 further comprising a sample containing inositol phosphorylceramide synthase.

13. The kit of claim 12 further comprising a known modulator of IPC synthase.

* * * * *